United States Patent [19]

Ramprasad et al.

[11] Patent Number: 4,680,037
[45] Date of Patent: Jul. 14, 1987

[54] LACUNAR COBALT COMPLEXES FOR OXYGEN SEPARATION

[75] Inventors: Dorai Ramprasad, Allentown, Pa.; Daryle H. Busch, Columbus, Ohio

[73] Assignee: Air Products and Chemicals, Inc., Allentown, Pa.

[21] Appl. No.: 900,935

[22] Filed: Aug. 28, 1986

[51] Int. Cl.⁴ .................................................. B01D 53/22
[52] U.S. Cl. ........................................... 55/16; 55/68; 55/158; 423/219; 423/579
[58] Field of Search ................ 55/16, 62, 68, 158; 423/219, 579

[56] References Cited

U.S. PATENT DOCUMENTS

| | | | |
|---|---|---|---|
| 2,450,276 | 9/1948 | Fogler et al. | 423/579 |
| 2,523,549 | 9/1950 | Axe | 423/219 X |
| 3,396,510 | 8/1968 | Ward, III et al. | 55/16 |
| 4,011,306 | 3/1977 | Fox, Jr. | 423/579 |
| 4,032,617 | 6/1977 | Gay | 423/219 |
| 4,343,715 | 8/1982 | Bonaventura et al. | 55/68 X |
| 4,421,530 | 12/1983 | Dalton, Jr. et al. | 55/62 X |
| 4,421,531 | 12/1983 | Dalton, Jr. et al. | 55/62 X |
| 4,427,416 | 1/1984 | Bonaventura et al. | 55/68 X |
| 4,451,270 | 5/1984 | Roman | 55/38 |
| 4,542,010 | 9/1985 | Roman | 423/579 |
| 4,584,359 | 4/1986 | Sterzel et al. | 526/241 |
| 4,602,987 | 7/1986 | Bonaventura et al. | 423/579 X |
| 4,605,475 | 8/1986 | Roberts et al. | 55/68 X |

OTHER PUBLICATIONS

D. H. Busch et al, "Molecular Species Containing Persistent Voids, Template Synthesis and Characterization of a Series of Lacunar-Nickel (II) Complexes and the Corresponding Free Ligands", J. Am. Chem. Soc., 1981, 103, pp. 1472–1478.

K. Kasuga et al, "The Preparation and Some Properties of Cobalt (II) Schiff Base Complexes and Their Molecular Oxygen Adducts", Bull. Chem. Soc. Jpn., 56, 95–98, (1983).

P. J. McCarthy et al, "inner Complex Chelates. I. Analogs of Bisacetylacetoneethylene Diimine and its Metal Chelates", J. Am. Chem. Soc., 1955, vol. 77, pp. 5820–5824.

Y-Y Chen et al, "High Spin Five-Coordinate Complexes of Cobalt (II), Nickel (II) and Copper (II) with Linear, Pentadante Keto Iminator Ligands", Inorg. Chem. 1981, 20, 1885–1892.

*Primary Examiner*—Robert Spitzer
*Attorney, Agent, or Firm*—Mark L. Rodgers; E. Eugene Innis; James C. Simmons

[57] ABSTRACT

The present invention is a cobalt complex having the structural formula:

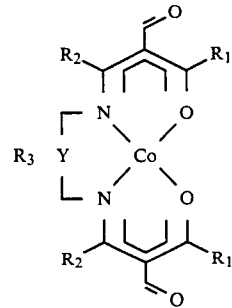

wherein each $R_1$ is independently hydrogen, a phenyl or a $C_1$–$C_6$ alkyl group; each $R_2$ is independently hydrogen or a $C_1$–$C_6$ alkyl group; $R_3$ is a $C_4$–$C_{30}$ hydrocarbyl radical connecting the two carbonyl carbons; and Y is o-phenylene, $-CH_2)_a$ wherein "a" is 2 or 3, $-CH_2)_b$N-$R_4$—$CH_2)_c$, wherein "b" and "c" are independently 2 or 3 and $R_4$ is hydrogen or a $C_1$–$C_{12}$ alkyl group.

These complexes have the ability to selectively and reversibly bind oxygen, thus making them useful components of oxygen separation membranes and absorbents.

26 Claims, No Drawings

4,680,037

LACUNAR COBALT COMPLEXES FOR OXYGEN SEPARATION

TECHNICAL FIELD OF THE INVENTION

The present invention relates to metal complexes that reversibly react with molecular oxygen and are suitable for use in air separation processes.

BACKGROUND OF THE INVENTION

Oxygen is produced industrially in enormous quantities from air. Currently, a majority of industrially-produced oxygen is separated from air by condensing the air and then fractionally distilling the liquid air to separate the oxygen from nitrogen and other gases. This liquefaction procedure consumes very large amounts of energy, since the boiling point of oxygen at atmospheric pressure is only 77° K.

In view of the known disadvantages of the air liquefaction process, attention has recently been directed toward methods for the separation of oxygen from air at temperatures much closer to ambient. In principle, such sepatation methods are very simple; a solution is prepared containing a compound which can complex molecular oxygen in a manner similar to that of the known biological oxygen-complexing proteins, myoglobin and hemoglobin, this solution is exposed to air or a similar oxygen-containing gas such that a large proportion of the oxygen-complexing compounds become complexed with oxygen. The solution is then removed from contact with the air and exposed to an environment induced by pressure or temperature changes in which the oxygen partial pressure is less than that in equilibrium with the oxygen-complexed compound, so that the compound gives up at least part of its oxygen, thereby releasing into the environment a gas much richer in oxygen than that with which the solution was originally in contact.

One technique for separating oxygen from air involves the use of "immobilized liquid membranes". Such immobilized liquid membranes comprise a solid support, typically a synthetic polymer which is inert to oxygen, together with liquid immobilized within the inert support. The support may have very fine pores therein so that the liquid is contained therein by capillary forces, a polymer film acting as the support may be swollen by contact with the liquid to form a gel or various other techniques may be used for immobilizing the liquid within the support. Air or some other oxygen-containing gas is passed over one side of the immobilized liquid membrane, while the gas which passes through the membrane is removed by pumping on the opposite side of the membrane. The oxygen "diffuses selectively" through the liquid membrane, due to the presence of an oxygen partial pressure gradient between the two sides of the membrane. The oxygen molecules are carried in the form of a metal complex through the immobilized liquid membrane at a much greater net transport rate than the rate in which other gases are passed through the membrane. One such membrane system is disclosed in U.S. Pat. No. 3,396,510 which discloses a facilitated transport system using a liquid membrane and a non-volatile species which is soluble in the immobilized liquid which reversibly reacts with a specific gaseous component to be separated from the gaseous mixture. Although the patent discloses the possibility of facilitated transport of oxygen, the proposed system is primarily an aqueous-based one, utilizing water soluble complexing agents, and was found to be commercially unfeasible. The carrier species disclosed in this patent include alkali bicarbonate, soluble arsenite salt, alkali sulfite, and other inorganic species.

Daryle H. Busch, et al. in an article entitled "Molecular Species Containing Persistent Voids. Template Synthesis and Characterization of a Series of Lacunar-Nickel Complexes in the Corresponding Free Ligands", in *J. Am. Chem. Soc.* 103 pp 1572–1478 (1981), discloses a family of lacunar ligands synthesized in the form of nickel (II) complexes by a template process. The species disclosed were designed to provide a "lacuna" or protective void, or cavity, in the vicinity of a coordination site in order to facilitate the binding of small molecules to the metal ions. The species of complexes are characterized by having four N-atoms bound to a single nickel atom, in a ligand system which results in an overall +2 charge for the complex.

Kuninobu Kasuga, et al. in an article entitled "A Preparation and Some Properties of Cobalt (II) Schiff-base Complexes and Their Molecular Oxygen Adducts", *Bull. Chem. Soc. Jpn.* 56, pp 95–98 (1983) disclose seven new cobalt (II) complexes with the tetradentate Schiff-base ligand and their three oxygen adducts. The disclosed complexes are reported to be stable at room temperature for several weeks and have the characteristic of having favorable affinity for molecular oxygen.

Roman, in U.S. Pat. Nos. 4,451,270 and 4,542,010 disclose processes and an apparatus for the separation and purification of oxygen and nitrogen. The processes utilize novel facilitated transport membranes to selectively transport oxygen from one gaseous stream to another, thereby leaving nitrogen as a by-product. In accordance with this process, an oxygen carrier capable of reversibly binding molecular oxygen is dissolved in a polar organic solvent and the resultant carrier solution is contained within a membrane which separates a gaseous feed stream, such as atmospheric air, to form a gaseous product stream. The oxygen carriers employed in the disclosed process are metal-containing complexes wherein a metal is bound by four ligating atoms, and has the capacity to reversibly bind oxygen and is also soluble in various polar organic solvents and reactive with axial bases.

U.S. Pat. No. 4,584,359 discloses a membrane of a vinyl polymer which contains oxygen-transferring groups not in solution, but in a chemically bonded form, which is used for separating molecular oxygen from a mixture of gases.

BRIEF SUMMARY OF THE INVENTION

The present invention is a class of lacunar cobalt complexes which are capable of reversibly reacting with molecular oxygen. The cobalt complexes have the general structural formula:

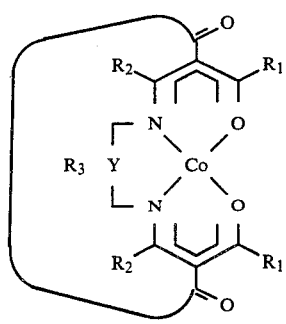

wherein each $R_1$ is independently hydrogen, a phenyl or a $C_1$–$C_6$ alkyl group; each $R_2$ is independently hydrogen or a $C_1$–$C_6$ alkyl group; $R_3$ is a $C_4$–$C_{30}$ hydrocarbyl radical connecting the two carbonyl carbons; and Y is o-phenylene, $-(CH_2)_a-$ wherein "a" is 2 or 3, $-(CH_2)_b N-R_4-(CH_2)_c-$, wherein "b" and "c" are independently 1, 2 or 3 and $R_4$ is hydrogen or a $C_1$–$C_{12}$ alkyl group.

The cobalt complexes described above have wide utility in oxygen separation operations. For example, the complex can be added to a solvent to form an oxygen absorption medium, or can be present as an $O_2$ carrier in a gas-separation membrane.

DETAILED DESCRIPTION OF THE INVENTION

The present invention is a new class of cobalt complexes which are useful in oxygen separation processes. The new class of complexes differ from prior art complexes in that the structures of the new complexes enable them to achieve relatively long life and good $O_2$ affinity at ambient temperatures.

The new class of cobalt complexes are lacunar Schiff base complexes having the general structural formula:

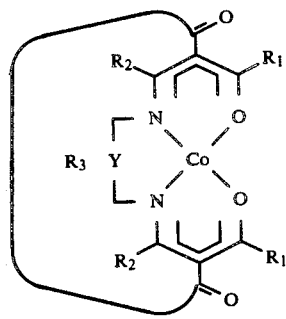

The structure is characterized by the presence of two keto-imine chelate ring moieties, joined by the linkage denoted by "Y" and having substituents $R_1$ and $R_2$. The substituent adjacent to each keto group, $R_1$, is independently hydrogen, a phenyl or a $C_1$–$C_6$ alkyl group. The substituent adjacent to the imine group on each keto-imine moiety, $R_2$, is independently hydrogen or a $C_1$–$C_6$ alkyl group. "Y" may either merely serve to link the two keto-imine moieties, in which case Y is either o-phenylene or $-(CH_2)_a-$ where "a" is 2 or 3; or Y may also contain a fifth ligating atom, in which case Y is $-(CH_2)_b NR_4-(CH_2)_c-$, wherein "b" and "c" are independently 1, 2 or 3 and $R_4$ is hydrogen or a $C_1$–$C_{12}$ alkyl group.

A critical component of the present structure is $R_3$, a $C_4$–$C_{30}$ hydrocarbyl radical which bridges between the two carbonyl carbons and provides the roof to the lacuna. $R_3$ can comprise a wide variety of structural components with the basic limitation being that the components form an unbroken "bridge" or "strap" between the two carbonyl carbons. Examples of suitable structural groupings for $R_3$ include: $C_4$–$C_{12}$ alkylene group, two or more phenylene groups, anthracene diradical, phenanthracene diradical or any combination thereof. Optionally, $R_3$ may also contain one or more heteroatoms such as S, N and O to provide flexible points in the bridge and for ease of synthesis. Specific examples of $R_3$ groups which incorporate one or more heteroatoms include:

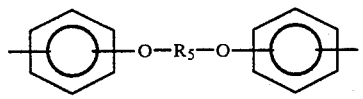

wherein $R_5$ is a $C_4$–$C_{12}$ alkylene group,

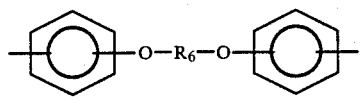

wherein $R_6$ comprises one or more phenylene groups, with or without one or more alkylene groups, and

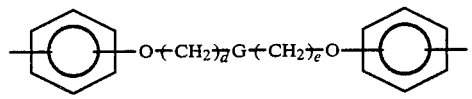

wherein "d" and "e" are each independently 0, 1, 2 or 3 and G is a substituted or unsubstituted heteroatom such as S, N or O.

While the phenylene-ether linkage present in the examples above are not necessary structural components, the presence of such groups on each carbonyl carbon is often preferred since the phenylene groups act as "risers", lifting the bridge above the plane of the Schiff base ligand, and the ether oxygen atoms facilitate the horizontal orientation of the rest of the bridging unit. Placement of the ether linkage at the meta position is preferred in that such position both limits its electron donating effect on the metal and also results in favorable orientation of the phenylene groups. While meta is preferred, ortho and para substituted phenylene groups are also suitable.

All of the above described groups may have one or more suitable organic or inorganic substituents such as methyl, ethyl, halogens, etc. The above structure provides a small, neutrally charged complex which allows for good diffusion characteristics. Additionally, the presence of the election-withdrawing groups adjacent to the carbonyl carbons increases the resistance of the complexes to autoxidation. Further, the "pocket" or "lacuna", formed by the $R_3$ groups, militates against formation of bridged peroxy compounds which form irreversibly in previously known Schiff-base oxygen complexes.

The present cobalt complexes reversibly bond oxygen, and because of their favorable longevity and diffusion characteristics, are well suited for use in a wide variety of oxygen separation processes. Specifically, the complexes can be used in the presence of a solvent as a selective absorbent for oxygen to separate oxygen from other gaseous components; e.g., nitrogen, argon, etc. Alternatively, the complexes can be used as mobile $O_2$ carriers in gas-separation membranes. One specific embodiment comprises an immobilized liquid membrane containing the oxygen carrier as a mobile species.

An oxygen-containing gas mixture is brought into contact with the cobalt complex for a time sufficient for at least a portion of the oxygen to bind with the complex. The bound oxygen is subequently released from the complex and recovered as product. The oxygen can be released by various means such as pressure differential, temperature differential, or any other suitable means. In cases in which the cobalt complexes are incorporated into membrane structures, the oxygen is transported across the membrane and subsequently released on the side opposite the feed.

In addition to the longevity and diffusion properties, the most fundamental property of the complex is oxygen affinity, as expressed by the equilibrium binding constant, $KO_2$, for the reaction:

$$LnCo + O_2 \underset{}{\overset{KO_2}{\rightleftarrows}} LnCo-O_2$$

wherein LnCo represents the cobalt complex.

Typically $KO_2$ is expressed as K (torr$^{-1}$) which is calculated:

$$K = \frac{[LnCo - O_2]}{P_{O_2}[LnCo]} = \frac{1}{\frac{P_{\frac{1}{2}O_2}}{2}} \text{ (torr}^{-1})$$

The value for K therefore is the reciprocal of the pressure at which ½ of the available complex will be bound with oxygen at a given temperature.

The cobalt complexes of the present invention have good oxygen affinity e.g., K (torr$^{-1}$) between $10^{-1}$ and $10^{-3}$ at ambient temperature and pressure, and also exhibit good oxygen affinity at varying conditions.

The present oxygen complexes can be used as oxygen absorbents in any suitable solvent. Solvents found to be useful in the present invention are generally organic liquids or mixtures of organic liquids which are preferably polar, although non-polar liquids may be useful in some cases. In other cases, the solvent may comprise a mixture of organic liquids in water. The solvent must be able to dissolve a sufficient concentration; e.g., preferably in excess of 0.05M, of the complex. Classes of useful solvents include: lactones, lactams, sulfoxides, nitriles, amides, amines, esters, ethers and other nitrogen-containing liquids. In cases in which the cobalt complex in solution has a structure wherein "Y" does not contain a N-atom, an "axial-base" may have to be added to the solution. Such axial-bases provide an additional coordinating atom to those contained in the oxygen carrier, which assists in the reversible binding of the oxygen. Classes of axial bases found useful are imidazoles, ketones, amides, amines, sulfoxides, peridenes, etc. In some instances, the solvent itself may be an axial base; e.g., acetonictrile.

Although the two most common applications for the present complexes are in membrane structures or in solution as absorbents, their stability makes them suitable for other possible applications, such as for instance in "air" batteries where gaseous $O_2$ forms part of one electrode.

Synthesis of the cobalt complex is typically carried out by preparing a precursor nickel compund wherein nickel is bound to two oxygen and two nitrogen atoms. The precursor compound then undergoes demetallization to remove the nickel and form a free ligand. The free ligand is subsequently reacted with a source of cobalt to form the cobalt complex. Examples 1-7 below illustrate specific techniques for synthesizing various cobalt complexes and the use of these complexes in binding oxygen. These examples are only illustrative and are not meant to limit the scope of the present invention.

EXAMPLES

Various lacunar cobalt complexes as described above were synthesized. Initially three different precursor complexes (I, II and III) were prepared having the structural formula:

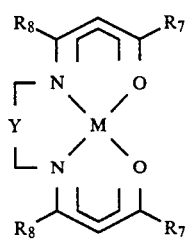

wherein $R_7 = CH_3; R_8 = H; Y = (CH_2)_2; M = Ni$ (I)

$R_7 = R_8 = CH_3; Y = (CH_2)_2; M = Ni$ (II)

$R_7 = R_8 = CH_3; Y = (CH_2)_3-\overset{Me}{\underset{|}{N}}-(CH_2)_3; M = Cu.$ (III)

The precursors were formed by known literature routes, such as taught by L. Wolf, et al. *Anorg. Allg. Chem.*, 1966, 346, 76; Y. Chen, et al. *Inorg. Chem.*, 20, 1885 (1981) and P. J. McCarthy, et al. *J. Am. Chem. Soc.* 1955, 77, 5820.

Acid chlorides, having the general structure:

$$Cl-C_6H_4-O-(CH_2)_z-O-C_6H_4-Cl$$

wherein z=6, 8 or 10 were also prepared. Meta substituted acid chlorides were prepared by a new reaction procedure which is described in detail below, while para substituted acid chlorides were prepared in accordance with the procedures disclosed by N. Webster, et al. *J. Chem. Research*, (M), 1978, 4855-4863.

Generally, four main steps are involved in synthesizing the lacunar cobalt complexes of the present invention. These steps include:
(a) Preparation of the acid chloride
(b) Preparation of the nickel complex
(c) Demetallation of the nickel complex
(d) Conversion of the free ligand into the cobalt complex

EXAMPLE 1

Synthesis of a Lacunar Cobalt Complex Wherein:

$R_1=CH_3; R_2=H; Y=(CH_2)_2.$ $R_3=C_6H_4-O-(CH_2)_8-O-C_6H_4-$ (a) Preparation of the C₈ Acid Chloride (z=8)

6.66 gm (0.289 mole) of sodium was dissolved in 350 ml of ethanol. To this, 20 gm (0.145 mole) of m-hydroxybenzoic acid was added with stirring until all the acid had dissolved. 1,8-dibromooctane (19.69 gm, 0.072 mole) was added and the mixture was refluxed overnight. A white precipitate was observed and this was filtered. The precipitate was dissolved in water, and concentrated hydrochloric acid was added until the solution was acidic. The C₈ dicarboxylic acid that precipitated was filtered. The carboxylic acid was redissolved in concentrated potassium hydroxide solution and then reprecipitated by the addition of concentrated hydrochloric acid. The precipitate was filtered, washed and dried in "vacuo" for several days until the solid was crusty. This crusty white solid was recrystallized from hot dioxane to obtain (6.5 gm, 0.017 mole), 23% yield of the C₈ dicarboxylic acid. The acid was refluxed with an excess of thionyl chloride. After two hours, all the solid was observed to dissolve to give a yellow solution. The thionyl chloride was distilled off to get a dark yellow oil. Benzene was added and the solution was rotovaped to dryness. This procedure was repeated once more. The contents of the flask were extracted with hot hexane which on cooling gave the C₈ acid chloride (4.4 gm. 0.01 mole), 61% yield.

(b) Preparation of the Nickel Complex 0.90 gm (3.56 mmole) of the precursor nickel complex [$R_1$=CH₃, $R_2$=H; Y=$\text{-(CH}_2\text{)}_2$] and 1.53 gm (3.63 mmole) of the C₈ acid chloride synthesized above were dissolved in 1500 ml of dry benzene containing 1.5 ml of triethylamine. The solution was refluxed for 6 days, and 1 ml of triethylamine was added after every 2 days. The triethylamine hydrochloride was filtered and the solvent was removed by rotary evaporation. The oily orange-red solid was dissolved in a minimum of chloroform and chromatographed on an alumina column. The fast moving orange-red band was collected on elution with chloroform. An orange-red solid was obtained by the addition of ethanol and reducing the volume of the solvent. This solid was recrystallized from methylene chloride and petroleum ether to give about 0.60 gm (1 mmole, 28% yield) of the lacunar nickel complex.

(c) Demetallation of the Nickel Complex 0.30 gm (0.45 mmole) of the lacunar nickel complex wws suspended in acetonitrile. To this, 0.17 gm (0.90 mmole) of p-toluenesulfonic acid was added. The solution was warmed gently until all the solid dissolved and the solution was green. The solution was reduced to dryness by rotary evaporation. Water was added to precipitate a pale yellow solid. After filtration, this solid was dissolved in chloroform, and the solution was dried over anhydrous sodium sulfate. The chloroform was removed by rotary evaporation. The contents of the flask were dissolved in a minimum of methylene chloride. Mixtures of ether and petroleum ether were added, and the solution was allowed to evaporate slowly in a fume cupboard to give 0.10 gm (0.18 mmole, 40% yield) of the ligand.

(d) Conversion of the Free Ligand into the Cobalt Complex 0.1 gm (0.18 mmole) of the free ligand was added to 0.05 gm of cobalt acetate hydrate and two equivalents of sodium hydroxide in methanol under an inert atmosphere. On refluxing for fifteen minutes, the color of the solution turned orange. After filtering and reducing the volume of the solvent, the lacunar cobalt complex was obtained as a yellow powder having a yield of about 40 mg or 37%.

EXAMPLE 2

Syntheses of a Lacunar Cobalt Complex Wherein:

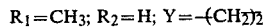
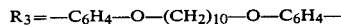

(a) Preparation of the C₁₀ Acid Chloride, (z=10)

10.1 gm (0.073 mole) of a m-hydroxybenzoic acid was dissolved in an ethanolic solution containing 3.55 gm (0.154 mole) of sodium. To this, 10.97 gm (0.036 mole) of 1,10-dibromodecane was added and the solution was refluxed overnight. The white precipitate that formed was filtered and dissolved in water and the C₁₀ dicarboxylic acid was precipitated by the addition of concentrated hydrochloric acid. The acid was purified by dissolving in potassium hydroxide solution and reprecipitating by the addition of concentrated hydrochloric acid. The carboxylic acid, after drying, was recrystallized from hot dioxane to obtain ≈4.5 gm (0.011 mole, 30% yield). 1.7 gm (0.004 mole) of the acid was suspended in 100 ml of benzene. 10 ml of thionyl chloride was added and the solution was refluxed until all the solid dissolved to give a yellow solution. The thionyl chloride and benzene were distilled off to give an oily solid. This was extracted with hot hexane to obtain 0.4 gm (0.001 mole, 25% yield) of the C₁₀ acid chloride.

(b) Preparation of the Nickel Complex 0.82 gm (3.24 mmole) of the precursor nickel complex, [$R_1$=CH₃; $R_2$=H; Y=$\text{-(CH}_2\text{)}_2$] was mixed with 1.5 gm (3.32 mmole) of C₁₀ acid chloride in 1000 ml of benzene containing 1 ml of triethylamine. After refluxing for 5 days, the solution was filtered to remove triethylamine hydrochloride. The solvent was removed on a rotary evaporator, and the residue was dissolved in a minimum of chloroform. Upon loading the sample on an alumina column, a fast moving orange-red band was eluted with chloroform. Ethanol was added and the solvent was evaporated until solid began to precipitate. The solution was filtered and cooled to obtain the lacunar nickel complex as an orange solid (0.25 gm, 0.39 mmole, 12% yield).

(c) and (d) The same demetallation and conversion steps as described in Example 1 above were carried out to form the final lacunar cobalt complex.

EXAMPLE 3

Syntheses of a Lacunar Cobalt Complex Wherein:

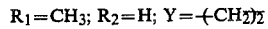
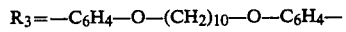

(a) Preparation of the C₆ Acid Chloride (z=8)

6.66 g (0.289 mole) of sodium was dissolved in 350 ml of ethanol. To this, 20 gm (0.145 mole) of m-hydroxybenzoic acid was added with stirring until all the acid had dissolved. 1,6-dibromohexane (17.66 g, 0.072 mole) was added and the mixture was refluxed overnight (14 hours). A white precipitate was observed and this was filtered. The precipitate was dissolved in water, and concentrated hydrochloric acid was added until the solution was acidic. The C₆ dicarboxylic acid that precipitated, was filtered. The purification was conducted in two steps. The carboxylic acid was redissolved in concentrated potassium hydroxide solution and then reprecipitated by the addition of concentrated hydrochloric acid. The precipitate was filtered, washed several times with water and dried in "vacuo" for several days until the solid was crusty. This crusty solid was recrystallized from hot dioxane to obtain 7.5 gm (0.021 mole, 29% yield). 7.5 gm (0.021 mole) of the $C_6$ dicarboxylic acid was suspended in 200 ml of thionyl chloride and refluxed. After 8 hours, all the solid was observed to dissolve to give a yellow solution. The thionyl chloride was distilled until a dark oil remained as a residue. Benzene was added to the dark oil, and the solvent was removed on a rotary evaporator. The solid residue was dissolved in dichloromethane and then reprecipitated by the addition of hexane and the reduction of the solvent volume on a rotary evaporator. The solid was filtered and then extracted with boiling hexane several times and, on cooling, the $C_6$ acid chloride separated as a white solid (2.3 gm, 0.006 mole, 28% yield).

(b) Preparation of The Lacunar Nickel Complex 0.9 gm (3.56 mmole) of the precursor nickel complex [$R_1$=$CH_3$; $R_2$=H; $Y$=—$(CH_2)_2$—] and 1.4 gm (3.54 mmole) of the $C_6$ acid chloride were dissolved in one liter of dry benzene containing 5 ml of triethylamine. After refluxing for six days, the solution was filtered to remove triethylamine hydrochloride. After removing the solvent by rotary evaporation, the solid was dissolved in a minimum volume of chloroform and chromatographed on an alumina column. A fast moving orange-red band was collected by elution with chloroform. An orange-red powder was obtained by the addition of ethanol and reducing the volume of the solvent. The sample was recrystallized from chloroform and petroleum ether to give 0.15 gm (0.26 mmole, 7%) of the lacunar $C_6$ complex.

(c) and (d) The same demetallation and conversion steps as described in Example 1 steps (c) and (d) above were carried out to form the final lacunar cobalt complex.

EXAMPLE 4

Synthesis of a Lacunar Cobalt Complex, Wherein:

$R_1$=$R_2$=$CH_3$; $Y$=—$(CH_2)_2$—;
$R_3$=—$C_6H_4$—O—$(CH_2)_8$—O—$C_6H_4$—

(a) Preparation of the Lacunar Nickel Complex 1.7 gm (6.5 mmole) of the precursor nickel complex, [$R_1$=$R_2$=$CH_3$; $Y$=—$(CH_2)_2$—] and 2.7 gm (6.38 mmole) of the $C_8$ acid chloride [prepared as described in Example 1 step (a)] were dissolved in 2 liters of dry benzene containing 3 gm of triethylamine. The mixture was refluxed for ten days and then filtered to remove triethylamine hydrochloride. The solvent was removed on a rotary evaporator, and the resulting solid was chromatographed on an alumina column. An orange-red band was eluted with chloroform and a red solid was crystallized from mixtures of chloroform and hexane.

Yield: 2.3 gm, 3.65 mmole, 60%

(b) Isolation of the Free Ligand 2 gm (3.17 mmole) of the lacunar nickel complex was reacted with 1.2 gm (6.30 mmole) of p-toluene sulfonic acid in acetonitrile with gentle warming until the solution turned green. The solvent was removed by rotary evaporation, and water was added to precipitate a yellow-white solid. This was filtered and dissolved in chloroform. Anhydrous sodium sulfate was added to produce a clear yellow solution. The solution was concentrated to a low volume, and petroleum ether was added to precipitate an oily solid. The solution was then decanted and rotovaped to dryness. Chloroform was added, followed by a large excess of ether and then petroleum ether to turn the solution cloudy. Slow evaporation resulted in 0.8 gm (1.4 mmole) of product, 44% yield.

(c) Formation of the Lacunar Cobalt Complex 0.8 gm (1.4 mmole) of the ligand was added to 0.4 gm (1.6 mmole) of cobalt acetate and 0.15 gm (3.75 mmole) of sodium hydroxide in 50 ml of methanol. On stirring and refluxing under an inert atmosphere for 30 minutes, a yellow precipitate was obtained. This was filtered and recrystallized from chloroform and pentane, producing 0.4 gm of the cobalt lacunar complex (45% yield).

EXAMPLE 5

Synthesis of a Lacunar Cobalt Complex Wherein:

$R_1$ = $R_2$ = $CH_3$; $R_3$ = —$C_6H_4$—O—$(CH_2)_6$—O—$C_6H_4$—

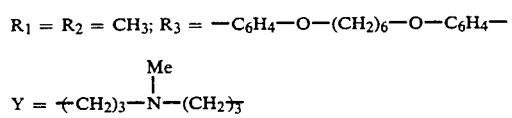

In a three necked two liter flask was placed 1500 ml of dry benzene containing 1 ml of triethylamine. 0.926 gm (2.5 mmole) of the precursor copper complex (III) was dissolved in 100 ml of dry benzene and placed in one dropping funnel. A solution of 0.988 gm (2.5 mmole) of the $C_6$ acid chloride in 100 ml of benzene was placed in another funnel. The two solutions were added dropwise, simultaneously, over a period of 48 hours, into the reservoir. After a period of 15 days, the solution was concentrated to a volume of 50 ml, and the addition of cyclohexane gave a precipitate. After filtering the precipitate, the resulting solution was rotovaped to dryness and the residue was dissolved in chloroform. Hydrogen sulfide gas was bubbled into this solution for several minutes. The copper sulfide was filtered using celite, and the filtrate was concentrated to a low volume. Addition of petroleum ether resulted in precipitate of the ligand as a powder.

Demetallation and conversion steps as set out in steps (c) and (d) of Example 1 above were carried out to convert the copper ligand to the desired cobalt complex.

All of the above synthesized compounds were satisfactorily characterized by a combination of $^{13}C$ NMR, infrared and mass-spectral and elemental analysis as appropriate.

EXAMPLE 6

To demonstrate the utility of the present cobalt complexes for binding oxygen, a complex having the structure wherein:

$R_1$ = $CH_3$; $R_2$ = H; $Y$ = —$(CH_2)_2$—; and $R_3$ = —$C_6H_4$—O—$(CH_2)_8$—O—$C_6H_4$— was dissolved in a solution containing 1% pyridine in toluene. The solution was contacted with a stream containing nitrogen and oxygen at ambient temperature. The binding constants ($K_{O_2}$) with oxygen for the complex were calculated, and the results are reported below.

| Wavelength* (nm) | $KO_2$ (torr$^{-1}$) | Standard Deviation |
|---|---|---|
| 500 | $9.43 \times 10^{-3}$ | $4.48 \times 10^{-4}$ |
| 540 | $9.96 \times 10^{-3}$ | $4.52 \times 10^{-4}$ |
| 580 | $9.68 \times 10^{-3}$ | $4.53 \times 10^{-4}$ |

*Wavelength of light used to measure the concentration of oxygenated and unoxygenated complex.

A $KO_2$ of $9.43 \times 10^{-3}$ (torr$^{-1}$) =

$P_{1/2}(O_2) = 1/0.00943 = 106$ torr.

This result indicates that at 27° C., ½ of the complex will be bound with oxygen at a pressure of 106 torr. Increasing the pressure will result in more oxygen being bound while decreasing the pressure will cause the oxygen to be released. Since atmospheric pressure is about 160 torr, it can be seen that the present cobalt complexes can be used to absorb oxygen at ambient temperature without requiring extreme high and low pressures to bind and release the oxygen, respectively.

EXAMPLE 7

A cobalt complex having the same structure wherein:

$R_1 = CH_3$; $R_2 = CH_3$; $Y = (CH_2)_2$; and $R_3 = -C_6H_4-O(CH_2)_8O-C_6H_4-$ was dissolved in a solution of 2%, 4,t-Butyl Pyridine in toluene. The solution was contacted with a stream containing nitrogen and oxygen at $-11.2°$ C., and the binding constants ($KO_2$) were measured. The results are reported below:

| Wavelength (nm) | $KO_2$ (torr$^{-1}$) | Standard Deviation |
|---|---|---|
| 330 | 7.06 | 1.25 |
| 350 | 6.51 | 1.17 |
| 360 | 7.63 | 0.72 |
| 370 | 8.39 | 0.68 |

As can be seen from the results above, at low temperatures, the cobalt complex has a strong affinity for oxygen; e.g., a pressure of only about 0.15 torr is required to bind ½ of the oxygen at $-11.2°$ C. This indicates that the selective binding and releasing of oxygen by these complexes can be regulated by using temperature differentials, or a combination of temperature and pressure changes, both well within feasible limits.

Having thus described the present invention, what is now deemed appropriate for Letters Patent is set out in the following appended claims.

What is claimed is:

1. A cobalt complex having the structural formula:

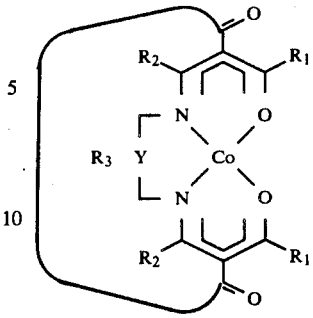

wherein each $R_1$ is independently hydrogen, a phenyl or a $C_1$-$C_6$ alkyl group; each $R_2$ is independently hydrogen or a $C_1$-$C_6$ alkyl group; $R_3$ is a $C_4$-$C_{30}$ hydrocarbyl radical connecting the two carbonyl carbons; and Y is o-phenylene, $(CH_2)_a$ wherein "a" is 2 or 3, $(CH_2)_bN$-$R_4(CH_2)_c$, wherein "b" and "c" are independently 1, 2 or 3 and $R_4$ is hydrogen or a $C_1$-$C_{12}$ alkyl group.

2. A cobalt complex in accordance with claim 1 wherein $R_3$ is a $C_4$-$C_{12}$ alkylene group.

3. A cobalt complex in accordance with claim 1 wherein $R_3$ contains one or more heteroatoms.

4. A cobalt complex in accordance with claim 3 wherein said heteroatoms are selected from the group consisting of S, N, O and mixtures thereof.

5. A cobalt complex in accordance with claim 4 wherein $R_3$ has the structural formula:

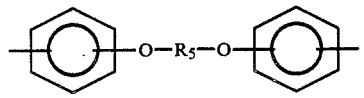

wherein $R_5$ is a $C_4$-$C_{12}$ alkylene group.

6. A cobalt complex in accordance with claim 5 wherein $R_3$ has the ether linkages in the meta position.

7. A cobalt complex in accordance with claim 5 wherein $R_1$ is $CH_3$ and $R_2$ is H.

8. A cobalt complex in accordance with claim 7 wherein Y is $(CH_2)_2$.

9. A cobalt complex in accordance with claim 4 wherein $R_3$ has the structural formula:

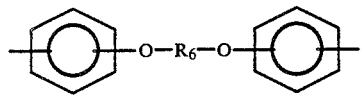

wherein $R_6$ comprises one or more phenylene groups.

10. A cobalt complex in accordance with claim 9 wherein $R_6$ also comprises one or more alkylene groups.

11. A cobalt complex in accordance with claim 1 wherein $R_3$ has the structural formula:

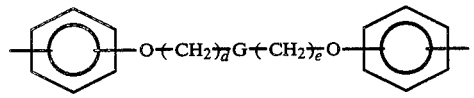

wherein "d" and "e" are each independently 0, 1, 2 or 3 and G is a substituted or unsubstituted heteroatom.

12. A cobalt complex in accordance with claim 11 wherein $R_3$ has the ether linkage in the meta position.

13. A cobalt complex in accordance with claim 1 wherein said complex is neutral in charge.

14. A cobalt complex in accordance with claim 1 wherein said complex has the capacity to selectively and reversibly bind oxygen.

15. A method for separating oxygen from a gaseous mixture comprising oxygen and at least one other component, said method comprising: bringing said gaseous mixture into contact with a cobalt complex having the structural formula:

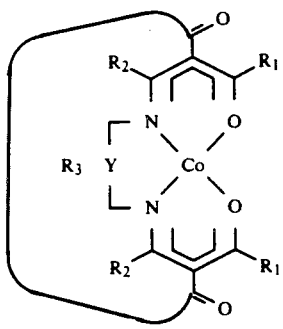

wherein each $R_1$ is independently hydrogen, a phenyl or a $C_1$-$C_6$ alkyl group; each $R_2$ is independently hydrogen or a $C_1$-$C_6$ alkyl group; $R_3$ is a $C_4$-$C_{30}$ hydrocarbyl radical connecting the two carbonyl carbons; and Y is o-phenylene, $-(CH_2)_a-$ wherein "a" is 2 or 3, $-(CH_2)_b-N-R_4-(CH_2)_c-$, wherein "b" and "c" are independently 1, 2 or 3 and $R_4$ is hydrogen or a $C_1$-$C_{12}$ alkyl group, such that at least a portion of the oxygen present in the gaseous mixture is reversibly bound to said cobalt complex.

16. A method in accordance with claim 15 wherein said bound oxygen is subsequently released from said cobalt complex and recovered as product.

17. A method in accordance with claim 15 wherein said cobalt complex is present as an $O_2$ carrier in a gas-separation membrane.

18. A method in accordance with claim 17 wherein said membrane comprises a liquid medium containing the cobalt complex as a mobile species.

19. A method in accordance with claim 15 wherein said cobalt complex is present in a solvent to form an absorbent solution.

20. A method in accordance with claim 19 wherein an axial base is also added said solvent.

21. A method in accordance with claim 19 wherein said solvent also functions as an axial base.

22. A method in accordance with claim 15 wherein said gaseous mixture is brought into contact with the cobalt complex at about ambient temperature.

23. A method in accordance with claim 22 wherein said oxygen-containing gaseous mixture also contains nitrogen and argon.

24. A method in accordance with claim 15 wherein said cobalt complex contains one or more heteroatoms.

25. A method in accordance with claim 24 wherein said cobalt complex has a structural formula wherein $R_3$ is:

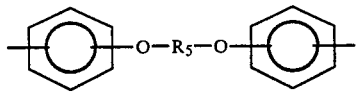

wherein $R_5$ is a $C_4$-$C_{12}$ alkylene group.

26. A method in accordance with claim 25 wherein said cobalt complex has a structural formula wherein $R_3$ has the ether linkages in the meta position.

* * * * *